(12) United States Patent
Savin-Poncet et al.

(10) Patent No.: US 6,355,150 B1
(45) Date of Patent: Mar. 12, 2002

(54) ANALYZER FOR MEASURING $H_2S$ AND ITS USE FOR A SULFUR OXIDATION REACTOR

(75) Inventors: Sabine Savin-Poncet, Buros; Andre Pepy, Lescar; Pierre Becourt, Bizanos, all of (FR)

(73) Assignee: Elf Exploration Production (FR)

( * ) Notice: Subject to any disclaimer, the term of this patent is extended or adjusted under 35 U.S.C. 154(b) by 0 days.

(21) Appl. No.: 09/462,722

(22) PCT Filed: May 10, 1999

(86) PCT No.: PCT/FR99/01099

§ 371 Date: Apr. 3, 2000

§ 102(e) Date: Apr. 3, 2000

(87) PCT Pub. No.: WO00/58950

PCT Pub. Date: Nov. 18, 1999

(30) Foreign Application Priority Data

May 12, 1998 (FR) .............................................. 98 05937

(51) Int. Cl.[7] .......................... G01N 27/404; G01N 1/22
(52) U.S. Cl. ........................ 204/409; 204/400; 204/431; 205/786.5

(58) Field of Search ................................. 204/400, 409, 204/410, 411, 431; 73/232, 23.31, 23.21; 205/786.5; 436/102, 120, 121, 179; 422/98

(56) References Cited

U.S. PATENT DOCUMENTS 3,888,109 A * 6/1975 Sharki et al. ................. 73/23.2
5,569,838 A * 10/1996 Broedel et al. ............. 73/23.31

* cited by examiner

*Primary Examiner*—Robert J. Warden, Sr.
*Assistant Examiner*—Kaj K. Olsen
(74) *Attorney, Agent, or Firm*—Townsend and Townsend and Crew LLP

(57) ABSTRACT

An analyzer for continuously measuring the $H_2S$ content of a gas stream which utilizes a drying module for drying the gas, a compressor for compressing the gas, a means for diluting the compressed sample and an electrical chemical sensor. The invention is also a device for regulating the flow rate of air to a $H_2S$ oxidation system which utilizes the analyzer to control the ratio of air to $H_2S$ stream entering the process.

21 Claims, 1 Drawing Sheet

ANALYZER FOR MEASURING $H_2S$ AND ITS USE FOR A SULFUR OXIDATION REACTOR

FIELD OF THE INVENTION

The invention relates to an analyser for continuously measuring the $H_2S$ contained in a gas. It also relates to a device including the said analyser for regulating the flow rate of air injected into a reactor for oxidizing $H_2S$ to sulphur.

BACKGROUND OF THE INVENTION

In order to recover the $H_2S$ present in low concentration, especially a concentration of less than 5% by volume, in gases of various origins, it is common practice to use processes involving oxidation, especially catalytic oxidation, of $H_2S$ to sulphur according to the reaction $H_2S + \frac{1}{2} O_2 \rightarrow S + H_2O$.

In such oxidation processes, the gas to be treated containing $H_2S$ in the presence of a controlled amount of a gas containing free oxygen is made to come into contact with a catalyst for selective oxidation of $H_2S$ to sulphur, the said contact being achieved at temperatures either above the dew point of the sulphur formed, in which case the sulphur formed is present in the vapor state in the gaseous effluent resulting from the reaction, or at temperatures below the dew point of the sulphur formed, in which case the said sulphur is deposited on the catalyst, thereby requiring the sulphur-laden catalyst to be periodically regenerated by purging, by means of a non-oxidizing gas having a temperature of between 200° C. and 500° C. The gas containing free oxygen used for oxidizing the $H_2S$ to sulphur is usually air, but it may also consist of oxygen, oxygen-enriched air or else mixtures, in various proportions, of oxygen and an inert gas other than nitrogen. In the following, "air" is used to denote the said gas containing free oxygen.

The amount of air, with which the gas to be treated containing $H_2S$ is combined, is continuously adjusted in response to a parameter resulting from the superposition of a prediction parameter, representative of an air flow rate corresponding to an amount of oxygen proportional to the amount of $H_2S$ present in the gas to be treated and injected into the oxidation reactor, and of a correction parameter (a feedback parameter), representative of a corrective air flow rate for bringing the $H_2S$ content present in the gaseous effluent coming from the oxidation back to a set value.

The oxidation is carried out in a reactor having an upstream end and a downstream end which are advantageously separated by a bed of a catalyst for selective oxidation of $H_2S$ to sulphur, the said upstream end being equipped with a first line and a second line for the injection of the gas to be treated and of air into the reactor, respectively, and the said downstream end being equipped with an output line for the gases, in order to discharge the gaseous effluent resulting from the oxidation, and the flow rate of air injected into the oxidation reactor is adjusted with the aid of a regulating device combining (i) a prediction unit, which comprises a prediction computer receiving a signal from a flow meter and a signal delivered by a first $H_2S$-content analyser, these being mounted in the first line at the upstream end of the oxidation reactor and generating, from the said signals, a signal representative of an air flow rate corresponding to an amount of oxygen proportional to the $H_2S$ content entering the oxidation reactor with (ii) a feedback unit, which comprises a correction computer receiving a signal delivered by a second $H_2S$-content analyser, mounted in the output line of the oxidation reactor and generating, from the said signal, a signal representative of a corrective air flow rate in order to bring the $H_2S$ content present in the gaseous effluent passing through the said output line back to a given set value and with (iii) a flow regulator, which receives the signals generated by the prediction and correction computers and the signal delivered by a flow meter, mounted in the air injection line at the upstream end of the oxidation reactor and applying, to a valve with an adjustable opening, mounted in the said air injection line downstream of the flow meter, a control signal for adjusting the opening of the said valve, the said control signal being the resultant of the signals generated by the prediction and correction computers.

The analysers, which are mounted in the line for injecting the gas to be treated into the oxidation reactor and on the output line of the said reactor, respectively, may be, for example, gas chromatography analytical units (U.S. Pat. No. 3,026,184 and FR-A-2,118,365), differential spectrometry analytical units (FR-A-2,420,754) or infrared absorption analytical units, after selective transformation of the $H_2S$ into $SO_2$.

The analysers of the aforementioned types, used for measuring the $H_2S$ content in gases containing this compound, do not always deliver continuous signals or do not always provide adequate sensitivity or adequate reliability, nor satisfactory operating simplicity.

SUMMARY OF THE INVENTION

The present invention provides an analyser for continuously measuring the $H_2S$ content of a gas containing it, which has a high sensitivity and the response of which shows no significant drift over time.

The analyser according to the invention, for continuously measuring the $H_2S$ content of a gas sample containing it, is characterized in that it comprises:

- a dry-operating module for drying the gas sample, comprising an inlet, connected to a nozzle for taking and injecting the said sample, and an outlet for the dried sample;
- a compressor module having a suction port, connected via a line to the outlet of the drying module, and a discharge port extended by a flow line for the compressed sample, the said line being equipped with an indicating and/or regulating primary flow meter;
- a system for diluting the compressed sample, comprising an air intake line, which is mounted as a branch off the flow line for the compressed sample, downstream of the primary flow meter, and which is equipped with a regulating secondary flow meter adjusting the degree of opening of a valve having an adjustable opening, mounted in the air intake line downstream of the secondary flow meter, and a regulating module connected to each of the primary and secondary flow meters and slaving the secondary flow meter to the primary flow meter; and
- an electrochemical sensor for measuring $H_2S$, which is mounted in the flow line for the compressed sample, downstream of the air intake line, and delivers a signal proportional to the concentration of $H_2S$ in the said sample.

Advantageously, the nozzle for taking and injecting the gas sample, connected to the inlet of the dry-operating module for drying the gas sample, may be provided, at its remotest end from the said inlet, with a primary filter. Optionally, a finer filter may be provided at the other end of the said nozzle, located on the same side as the said module.

If required, this nozzle may be surrounded by a jacket equipped with means for maintaining the temperature, for example by electrical heating or by the circulation of a heat-transfer fluid.

The dry-operating module for drying the gas sample may consist, in particular, of a dryer comprising permeation membranes such as the "SEC" dryer sold by Environnement SA.

The compressor module may be chosen from various miniaturized compressors having the required performance. Particularly suitable are diaphragm compressors.

The indicating and/or regulating primary flow meter mounted in the flow line for the compressed sample, as well as the regulating secondary flow meter mounted in the air intake line are, in particular, mass flow meters. In this case, the regulating module which is associated with them is a mass-regulating module.

The electrochemical sensor for measuring the $H_2S$ concentration is of the electrochemical transducer type for measuring the partial pressure of the compound measured. This sensor comprises a measurement cell, which contains a liquid electrolyte, in which a measurement electrode, a comparison electrode and a reference electrode are immersed, and which is separated, by a membrane, from the flow space for the gas sample on which the measurement is made. A constant electrical voltage is maintained between the measurement electrode and the reference electrode. The gas sample containing the compound to be measured, in the present case $H_2S$, diffuses through the membrane into the liquid electrolyte. The aforementioned electrical voltage, the electrolyte and the material of the electrodes are chosen so that the compound, the concentration of which is to be determined, is transformed electrochemically at the measurement electrode and so that an electric current of intensity proportional to the concentration of the said compound passes through the measurement cell. An electrochemical reaction occurs at the same time, at the comparison electrode, with the oxygen of the dilution air. Such a sensor delivers an electrical signal of intensity proportional to the concentration of the compound to be measured, in this case $H_2S$, present in the flowing gas sample in contact with the sensor. As an example of an electrochemical sensor that can be used in the analyser according to the invention, mention may be made of the sensor sold by Drager under the name "Polytron $H_2S$".

The analyser according to the invention, which allows the concentration of $H_2S$ contained, in relatively large amount, in a gas to be determined, is most particularly usable as an $H_2S$ analyser in an air-flow-regulating device with which a reactor for oxidizing $H_2S$ to sulphur is equipped. More especially, the analyser according to the invention can be used to form the analyser of a feedback unit and even the analyser of a prediction unit of the regulating device having the structure defined above, in order to regulate the flow rate of air injected into a reactor for oxidizing $H_2S$ to sulphur.

The invention will be more clearly understood on reading the description given below of one of its embodiments, made with reference to the appended drawings in which:

DETAILED DESCRIPTION OF THE INVENTION

Figure 1:
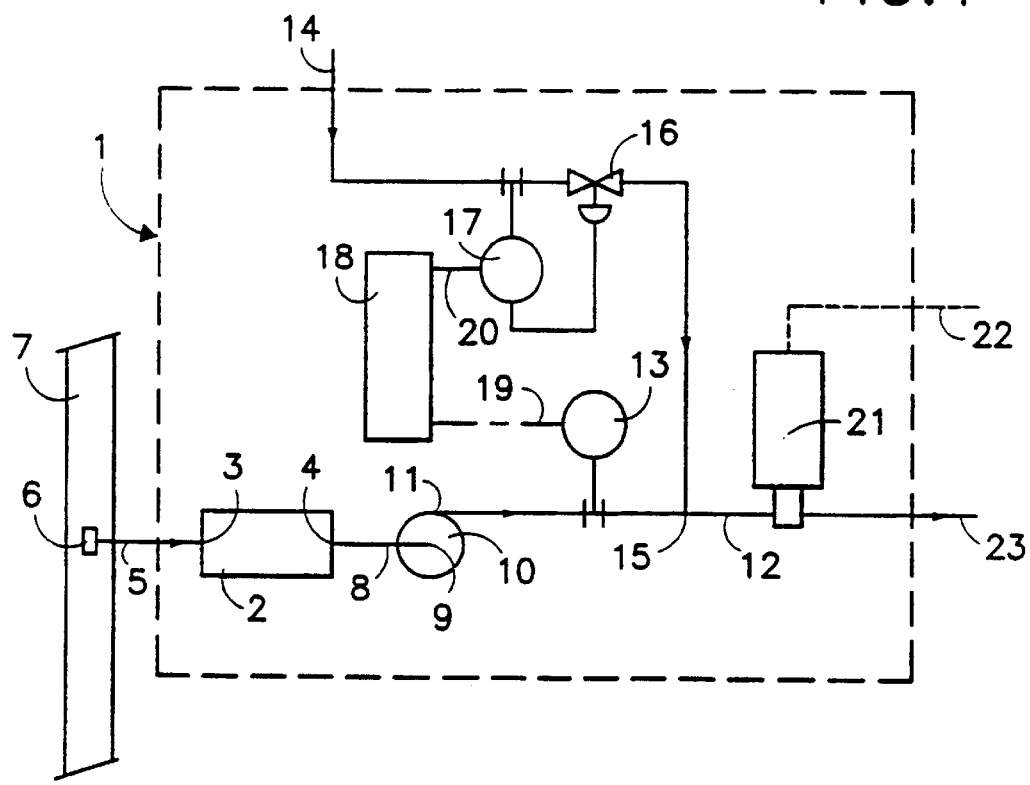
FIG. 1 gives a schematic representation of an analyser according to the invention.

Referring to FIG. 1, the analyser 1 illustrated comprises a permeation-membrane dryer 2 forming a dry-operating module for drying the gas sample, the said dryer having an inlet 3 and an outlet 4. The inlet 3 of the dryer is connected to a nozzle 5 for taking and injecting a gas sample. The end of the said nozzle, which is furthermost from the inlet of the dryer, is provided with a primary filter 6, namely a filter consisting of sintered material, and especially of ceramic, which retains the solid particles having a size greater than, for example, 20 $\mu$m, and penetrates the line 7 through which the gas to be sampled for analysis flows. At its end connected to the inlet of the dryer 2, the nozzle 5 is provided with a fine filter (not shown) which retains the solid particles having a size greater than 0.3 $\mu$m, for example.

The outlet 4 of the dryer 2 is connected via a line 8 to the suction port 9 of a diaphragm compressor 10 forming a compression module. The said compressor has a discharge port 11 which is extended by a gas flow line 12 on which an indicating and/or regulating primary mass flowmeter 13 is mounted. An air intake line 14 is mounted as a branch off the flow line 12 at a point 15 on the latter, located downstream of the flow meter 13, the said line 14 being provided with a valve 16, having an adjustable degree of opening, and with a regulating secondary mass flow meter 17 located upstream of the valve 16 and used for adjusting the degree of opening of the latter. A mass-regulating module 18 receives, via an electrical linkage 19, the signal delivered by the primary flow meter 13 and sends, via an electrical linkage 20, a signal to the said secondary flow meter 17 in order to slave the secondary flow meter 17 to the primary flow meter 13. The unit formed by the air intake line 14 with its valve 16 and the secondary flow meter 17 and by the mass-regulating module 18 constitutes a dilution system for the contents of the line 12.

An electrochemical sensor 21 for measuring the $H_2S$ concentration is mounted in the flow line 12, downstream of the point 15 where the air intake line 14 joins the flow line 12, the said sensor delivering a signal proportional to the measured $H_2S$ concentration via an electrical conductor 22.

That part of the nozzle 5 provided with the filter 6 and that part 23 of the line 12 located downstream of the sensor 21 form, respectively, the inlet of the analyser for the gas sample to be analysed and the outlet of the analyser for the said gas sample, while the conductor 22 constitutes the measurement output of the analyser.

Figure 2:
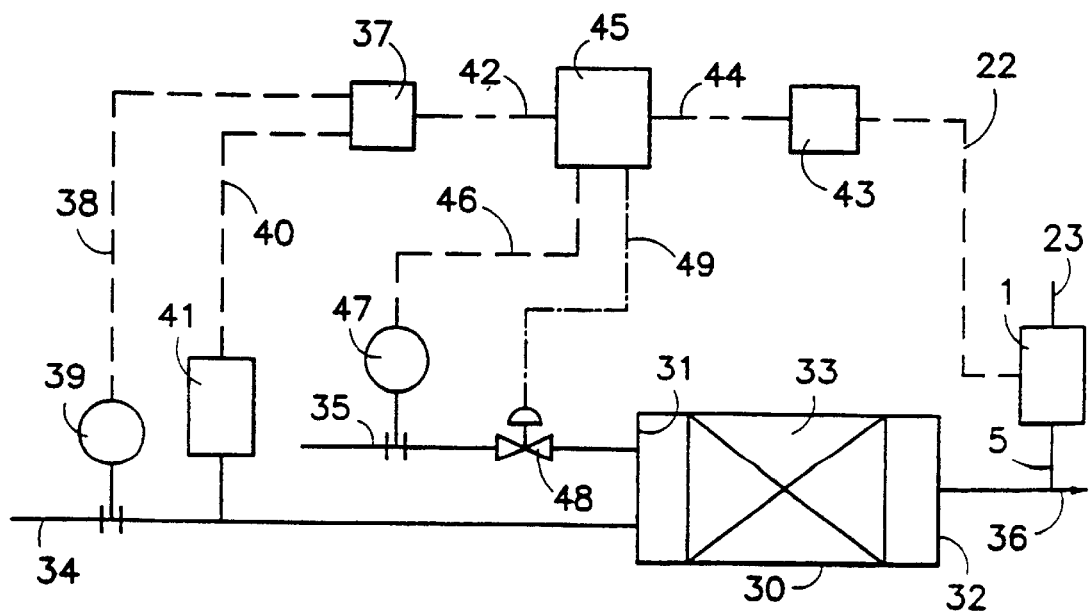
FIG. 2 shows schematically a reactor for oxidizing $H_2S$ to sulphur, equipped with a device for regulating the flow rate of air injected into the reactor, the said device including an analyser as illustrated in FIG. 1.

Referring to FIG. 2, a reactor 30 for oxidizing $H_2S$ to sulphur has an upstream end 31 and a downstream end 32 which are separated by a bed 33 of a catalyst for selective oxidation of $H_2S$ to sulphur, the said upstream end being equipped with a first line 34 and with a second line 35 for the injection of a gas to be treated containing $H_2S$ and of air into the reactor, respectively, and the said downstream end being equipped with an output line 36 for the gases, in order to discharge the gaseous effluent resulting from the oxidation.

The oxidation reactor is equipped with a device for regulating the flow rate of air injected into the oxidation reactor, the said regulating device consisting of the combination of a prediction unit, a feedback unit and an air flow regulator.

The prediction unit comprises a prediction computer 37 which receives a signal 38 from a flow meter 39 and a signal 40 delivered by a first $H_2S$-content analyser 41, these being mounted in the first line 34 located at the upstream end of the oxidation reactor 30, and which generates, from the said signals, a signal 42 representative of an air flow rate corresponding to an amount of oxygen proportional to the amount of $H_2S$ entering the oxidation reactor.

The feedback unit comprises a correction computer 43 which receives a signal 22 delivered by a second $H_2S$-content analyser 1, mounted in the output line 36 of the oxidation reactor, and which generates, from the said signal 22, a signal 44 representative of a corrective air flow rate in order to bring the content of the $H_2S$ present in the gaseous effluent flowing through the said output line back to a given set value.

The flow regulator 45 receives the signals 42 and 44, generated by the prediction computer 37 and the correction computer 43 respectively, and the signal 46 delivered by a flow meter 47, mounted in the air injection line at the upstream end of the oxidation reactor, and applies, to a valve 48 having an adjustable opening, mounted in the said air injection line downstream of the flow meter 47, a control signal 49 for adjusting the opening of the said valve, the said control signal being the resultant of the signals 42 and 44 generated by the prediction computer 37 and the correction computer 43, respectively.

The $H_2S$-content analyser 1, mounted in the output line 36 of the oxidation reactor, is an analyser having the structure of the analyser described above with reference to FIG. 1. The $H_2S$-content analyser 41, mounted in the first line 34 located at the upstream end of the oxidation reactor 30, may be an analyser similar to the analyser 1 or may consist of an analyser of another type, for example an infrared-absorption analyser, after the $H_2S$ has been selectively transformed into $SO_2$, a gas-chromatography analyser or a differential-spectrometry analyser.

The analyser according to the invention and the regulating device including it, which are described above, operate as indicated below.

A sample of the $H_2S$-containing gas to be analysed is taken from the output line 36 of the oxidation reactor 30, which corresponds to the line 7 shown in FIG. 1, via the nozzle 5, through the filter 6 and the said sample is injected, via the said nozzle maintained by electrical heating at a temperature of approximately 135° C., into the permeation-membrane dryer 2 in which the water vapor contained in the sample is almost completely removed. The dry gas sample is drawn into and compressed in the diaphragm compressor 10 and then sent into the flow line 12 in which, after it has passed through the primary mass flow meter 13, it is diluted by the injection of air entering via the line 14 with a mass flow rate which is slaved, by the action of the regulating module 18 acting on the regulating secondary flow meter 17 adjusting the degree of opening of the valve 16, to the mass flow rate of the sample measured by the flow meter 13. The flow rate of dilution air is chosen so that the $H_2S$ content of the diluted sample lies within the allowed concentration range for the sensor. Next, the diluted gas sample flows in contact with the electrochemical sensor 21 for measuring the $H_2S$ concentration of the said sample, after which the diluted sample is sent to a flare (not shown) in order to be burnt. The sensor 21 delivers an electrical signal 22 proportional to the $H_2S$ content of the sample analysed.

The prediction computer 37 receives, from the flow meter 39, a signal 38 representative of the flow rate of $H_2S$-containing gas injected into the oxidation reactor 30 and, from the analyser 41, a signal 40 representative of the $H_2S$ content of the said gas and it generates, from these signals, a signal 42 representative of an air flow rate corresponding to an amount of oxygen proportional to the amount of $H_2S$ entering the oxidation reactor. The coefficient of proportionality corresponds, in particular, to the molar ratio $O_2/H_2S$ chosen for carrying out the $H_2S$ oxidation, the said ratio possibly ranging, for example, from 0.5 to 10 and more particularly from 0.5 to 4. Advantageously, the coefficient of proportionality may be gradually increased during the oxidation step, for example from a value of 0.5 to a value of 4, in order to prevent gradual deactivation of the catalyst during the said step.

The correction computer 43 receives, from the analyser 1, a signal 22 representative of the $H_2S$ content of the gaseous effluent leaving the oxidation reactor 30 via the output line 36 and it generates, from the said signal, a signal representative of a corrective air flow rate in order to bring the content of the $H_2S$ present in the gaseous effluent flowing through the said output line back to a given set value.

The flow regulator 45 receives the signals 42 and 44 generated by the prediction computer 37 and the correction computer 43, respectively, and the signal 46 delivered by the flow meter 47, mounted in the air injection line 35 at the upstream end of the oxidation reactor 30, and it generates, from the said signals, a control signal 49 which it applies to the valve 48 with an adjustable opening, which is mounted in the said air injection line 35 downstream of the flow meter 47, in order to adjust the opening of the said valve, the said control signal 49 being the resultant of the signals 42 and 44 generated by the prediction computer 37 and the correction computer 43, respectively.

In an alternative embodiment, the line 34 supplying the $H_2S$-containing gas to the oxidation reactor is the output line of a hydrogenation and/or hydrolysis reactor in which a sulphur plant residue gas is treated in order to convert all the sulphur compounds that it contains into $H_2S$. In this case, instead of being placed in the said line 34, the flow meter 39 may be mounted in the line for feeding the sulphur plant residue gas into the hydrogenation and/or hydrolysis reactor.

We claim:

1. Analyser for continuously measuring the $H_2S$ content of a gas sample, said analyser comprising:
    a drying module (2) for drying the gas sample, comprising an inlet (3), connected to a nozzle (5) for taking and injecting the gas sample, and an outlet (4) for discharging a dried gas sample;
    a compressor module (10) having a suction port (9), connected via a line (8) to the outlet of the drying module, and a discharge port (11) coupled to a flow line (12) for discharging a compressed gas sample, the flow line (12) being equipped with an indicating and/or regulating primary flow meter (13);
    a system for diluting the compressed gas sample, comprising: an air intake line (14), which is mounted as a branch off the flow line (12) carrying the compressed gas sample, the air intake line being located downstream of the primary flow meter, the air intake line being equipped with a regulating secondary flow meter (17) for controlling the degree of opening of a valve (16) having an adjustable opening, mounted in the air intake line downstream of the secondary flow meter, the system including a regulating module (18) connected to each of primary and secondary flow meters; and
    an electrochemical sensor (21) for measuring $H_2S$, which is mounted in the flow line (12) downstream of the air intake line (14), the sensor generating an output signal (22) proportional to the concentration of $H_2S$ in the gas sample.

2. The analyzer according to claim 1, wherein the nozzle (5), connected to the inlet of the drying module (2) is provided, at its end opposite said inlet, with a primary filter (6).

3. The analyzer according to claim 2, wherein the end of the nozzle (5), located on the same side as the drying module (2), is equipped with a fine filter.

4. The analyser according to claim 3 wherein the end of the nozzle (5), for taking and injecting the gas sample is surrounded by a jacket equipped with means for maintaining the nozzle temperature by a heating means selected from the group consisting of electrical heating or circulation of a heat-transfer fluid.

5. The analyser of claim 3 wherein the dry-operating module (2) for drying the gas sample comprises a permeation-membrane dryer.

6. The analyser according to claim 2 wherein the end of the nozzle (5), for taking and injecting the gas sample is surrounded by a jacket equipped with means for maintaining the nozzle temperature by a heating means selected from the group consisting of electrical heating or circulation of a heat-transfer fluid.

7. The analyser according to claim 2 wherein the drying module (2) for drying the gas sample comprises a permeation-membrane dryer.

8. The analyser of claim 2 wherein the primary flow meter (13) mounted in the flow line (12) for the compressed sample, and the secondary flow meter (17) mounted in the air intake line (14), are mass flow meters.

9. Analyser according to claim 1, wherein the nozzle (5) for taking and injecting the gas sample is surrounded by a jacket equipped with means for maintaining the nozzle temperature, by a heating means selected from the group consisting of electrical heating or circulation of a heat-transfer fluid.

10. The analyser according to claim 9 wherein the drying module (2) for drying the gas sample comprises a permeation-membrane dryer.

11. The analyzer according to claim 1 wherein the drying module (2) for drying the gas sample comprises a permeation-membrane dryer.

12. The analyser according to claim 1, wherein the compressor module (10) is a diaphragm compressor.

13. The analyser according to claim 1, wherein the primary flow meter (13) mounted in the flow line (12) for the compressed sample, and the secondary flow meter (17) mounted in the air intake line (14), are mass flow meters.

14. The analyser according to claim 13, wherein the regulating module (18), associated with the primary flow meter (13) and with the secondary flow meter (17), comprises a mass-regulating module.

15. The analyser according to claim 1, wherein it is integrated, as an $H_2S$ analyser, into a device for regulating the flow rate of air injected into a reactor for oxidizing $H_2S$ to sulphur.

16. A device for regulating the flow rate of air injected into a reactor (30) for oxidizing $H_2S$ to sulphur, the reactor having an upstream end (31) and a downstream end (32), the upstream end of the reactor being equipped with a first line (34) for injection of gas to be treated into the reactor (30) and with a second line (35) for injection of air into the reactor, and the downstream end of the reactor being equipped with an output line (36) for discharging a gaseous effluent, said regulating device comprising
(i) a prediction unit, with comprises a prediction computer (37) receiving a first signal (38) from a first line flow meter (39) and a second signal (40) delivered by a first $H_2S$-content analyser, the first line flow meter (39) and first $H_2S$-content analyser for mounting in the first line (34) upstream of the reactor, the prediction unit generating, from the first and second signals, a third signal (42) representative of an air flow rate corresponding to an amount of oxygen proportional to the content of $H_2S$ entering the reactor (30),
(ii) a feedback unit, which comprises a correction computer (43) receiving an output signal (22) delivered by a second $H_2S$-content analyser (1), the second $H_2S$-content analyser (1) for mounting in the output line (36) of the reactor, the feedback unit generating, from the output signal, a fourth signal (44) representative of a corrective air flow rate in order to bring the content of the $H_2S$ present in the gaseous effluent flowing through the said output line back to a given set value and
(iii) a flow regulator (45) receiving the third and fourth signals (42, 44) generated by the prediction (37) and correction (43) computers and a fifth signal (46) delivered by a second line flow meter (47), for mounting in the second line (35) upstream of the reactor, and applying a control signal (49) to a valve (48) with an adjustable opening, which is mount,ed in the second line (35) downstream of the second line flow meter (47), a the control signal (49) for adjusting the opening of said valve, the control signal being the resultant of the third and fifth signals generated by the prediction and correction computers, and is characterized in that at least the second $H_2S$-content analyser (1), for mounting in the output line (36) of the reactor (30) and associated with the correction computer (43), is an analyser according to claim 1.

17. The regulating device according to claim 16, wherein the prediction computer (37) applies a coefficient of proportionality between the molar amount of oxygen and the molar amount of $H_2S$ ranging from 0.5 to 10 and more particularly from 0.5 to 4.

18. The regulating device according to claim 16 wherein the prediction computer (37) applies a coefficient of proportionality between the molar amount of oxygen and the molar amount of $H_2S$, said coefficient gradually increasing during oxidation.

19. The regulating device according to claim 16 wherein the first $H_2S$-content analyser (41) is also an analyser according to claim 1.

20. The regulating device according to claim 16, wherein the line (34), feeding the $H_2S$-containing gas into the oxidation reactor, is the output line of a hydrogenation and/or hydrolysis reactor in which a sulphur plant residue gas is treated in order to convert all the sulphur compounds that it contains into $H_2S$ and in that the flow meter (39), which is connected to the prediction computer (37) is mounted in the line for feeding the sulphur plant residue gas into the hydrogenation and/or hydrolysis reactor.

21. A device for regulating the flow rate of air injected into a reactor (30) for oxidizing $H_2S$ to sulphur, the reactor having a first line (34) for injection of gas to be treated into the reactor (30) and a second line (35) for injection of air into the reactor (30), the reactor having an output line (36) for discharging a gaseous effluent, the regulating device comprising:
(i) a prediction unit, which comprises a prediction computer (37) receiving a first signal (38) from a first line flow meter (39) and a second signal (40) delivered by a first $H_2S$-content analyser, the first line flow meter (39) and first $H_2S$-content analyser for mounting in the first line (34), the prediction unit generating a predictor signal (42) representative of an air flow rate corresponding to an amount of oxygen proportional to the content of $H_2S$ entering the reactor;
(ii) a feedback unit, which comprises a correction computer (43) receiving an output signal (22) delivered by a second H$_2$S-content analyser (1), the second H$_2$S-content analyser (1) for mounting in the output line (36), the feedback unit generating, from the output signal, a corrective signal (44) representative of a corrective air flow rate in order to bring the content of the H$_2$S present in the gaseous effluent flowing through the output line back to a given set value; and (iii) a flow regulator (45) receiving the predictor and corrective signals and a third signal (46) delivered by a second line flow meter (47) for mounting in the second line (35), the flow regulator (45) delivering a control signal (49) to a valve (48) for adjusting an adjustable opening of the valve (48), the valve (48) for mounting in the second line (35) downstream of the second line flow meter (47), the control signal (49) being the resultant of the predictor and corrective signals, and wherein at least the second H$_2$S-content analyser (1), for mounting in the output line (36) and being associated with the correction computer (43), is an analyzer according to claim 1.

* * * * *